(12) United States Patent
Wang et al.

(10) Patent No.: US 6,436,171 B1
(45) Date of Patent: Aug. 20, 2002

(54) OXYGEN-SELECTIVE ADSORBENTS

(75) Inventors: Qing Min Wang, North Plainfield; Dongmin Shen, Berkeley Heights; Miu Ling Lau, Edison; Martin Bülow, Basking Ridge; Frank R. Fitch, Bedminster; Norberto O. Lemcoff, Livingston, all of NJ (US); Philip Connolly, Philadelphia, PA (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 09/592,351

(22) Filed: Jun. 12, 2000

Related U.S. Application Data (60) Provisional application No. 60/145,130, filed on Jul. 22, 1999.

(51) Int. Cl.$^7$ .................. B01D 53/047; B01D 53/46
(52) U.S. Cl. .................. 95/96; 95/99; 95/138; 95/900; 96/108; 423/219
(58) Field of Search .............. 95/96–103, 138, 95/900; 96/108; 423/219

(56) References Cited

U.S. PATENT DOCUMENTS

| | | | |
|---|---|---|---|
| 2,450,276 A | | 9/1948 | Fogler et al. |
| 2,508,490 A | | 5/1950 | Calvin et al. |
| 4,514,522 A | | 4/1985 | Sievers et al. |
| 4,654,053 A | * | 3/1987 | Sievers et al. ............ 95/900 X |
| 4,800,188 A | | 1/1989 | Shepherd |
| 4,888,032 A | * | 12/1989 | Busch .................... 423/219 X |
| 4,952,289 A | * | 8/1990 | Ciccone et al. ......... 423/219 X |
| 4,985,053 A | * | 1/1991 | Sugie ...................... 423/219 X |
| 5,114,688 A | * | 5/1992 | Martell et al. ............. 423/219 |
| 5,126,466 A | * | 6/1992 | Ramprasad et al. ...... 95/138 X |
| 5,141,725 A | * | 8/1992 | Ramprasad et al. ........ 423/219 |
| 5,194,603 A | | 3/1993 | Tsuchida et al. |
| 5,208,335 A | | 5/1993 | Ramprasad et al. ........ 544/225 |
| 5,266,283 A | | 11/1993 | Friesen et al. .............. 423/219 |
| 5,294,418 A | | 3/1994 | Ramprasad et al. ........ 423/219 |
| 5,382,280 A | | 1/1995 | Choe et al. ..................... 95/98 |
| 5,721,187 A | | 2/1998 | Ogawa et al. .............. 502/417 |
| 5,735,938 A | | 4/1998 | Baksh et al. .................. 95/101 |
| 5,945,079 A | | 8/1999 | Mullhaupt et al. .......... 423/219 |
| 6,077,457 A | * | 6/2000 | Friesen et al. .......... 423/219 X |
| 6,136,222 A | * | 10/2000 | Friesen et al. .......... 423/219 X |
| 6,139,603 A | * | 10/2000 | Boisselier-Cocolios et al. .......... 95/138 X |
| 6,174,505 B1 | * | 1/2001 | Guilard et al. .............. 423/219 |
| 6,183,709 B1 | * | 2/2001 | Stephenson et al. .... 423/219 X |

FOREIGN PATENT DOCUMENTS

| | | |
|---|---|---|
| EP | 0 369713 A2 | 5/1990 |
| EP | 0 475 053 A1 | 3/1992 |
| EP | 0 711 598 A2 | 5/1996 |
| EP | 0 853 966 A1 | 7/1998 |
| EP | 0 853 968 A1 | 7/1998 |
| EP | 0 853 976 A1 | 7/1998 |

OTHER PUBLICATIONS

Guang Qing Li and Rakesh Govind, "Separation of Oxygen from Air Using Coordination Complexes: A Review," Ind. Eng. Chem. Res. 1994, 33, pp. 755–783.

* cited by examiner

*Primary Examiner*—Robert H. Spitzer
(74) *Attorney, Agent, or Firm*—Philip H. Von Neida; Salvatore P. Pace (57) ABSTRACT

The present invention provides for novel solid state $O_2$-selective metal complex-based adsorbents and their utility for separating oxygen from a gas stream. In particular, the invention provides for an adsorption complex which contains four-coordinate $O_2$-selective metal complexes including oligomeric/polymeric metal complexes, and organic base-containing polymers supported on porous materials.

21 Claims, 2 Drawing Sheets

OXYGEN-SELECTIVE ADSORBENTS

This application claims priority from Provisional Patent Application No. 60/145,130 filed Jul. 22, 1999.

FIELD OF THE INVENTION

The present invention is directed to novel solid state $O_2$-selective metal complex-based adsorbents and the processes for separating oxygen from air or other gas mixtures to produce high purity nitrogen and/or argon utilizing these adsorbents. In particular, the present invention relates to four-coordinate $O_2$-selective metal complexes including oligomeric/polymeric metal complexes, and those organic-inorganic hybrid $O_2$-selective adsorbents containing such metal complexes. Another feature of the adsorbents of the present invention is that four-coordinate $O_2$-selective metal complexes may be combined with organic base-containing polymers and porous supports.

BACKGROUND OF THE INVENTION

Two main complementary technologies are presently used in the air separation industry. They are the cryogenic and non-cryogenic processes. The cryogenic process supplies oxygen and nitrogen products as liquid and/or gas from centralized plants or small on-site plants. The non-cryogenic process includes pressure swing adsorption (PSA) or temperature swing adsorption, (TSA) and membrane separation to produce the gas products at ambient temperature from small on-site plants.

Presently, a number of $N_2$-selective synthetic zeolites and $O_2$-selective carbon molecular sieves are being used as solid adsorbents for non-cryogenic air separation. Synthetic zeolites and carbon molecular sieves (CMS) have been used in PSA processes for the production of either enriched nitrogen or oxygen. Recently, metal complex-based materials have been examined as possible candidates for $O_2$ selective adsorbents because they can reversibly adsorb oxygen at or below ambient temperatures. These types of materials may have significant advantages over known adsorbents because of their high selectivity to oxygen and the ease with which their molecular structures may be modified.

The utility of $O_2$-selective metal complex-based adsorbents has been disclosed for solutions of metal complexes, for solid-state metal complexes or their slurries, for metal complexes supported physically on solid porous materials, for metal complexes incorporated into zeolites, for metal complexes bound chemically to solid supports, and for facilitated metal complex-based membranes. However, each of these technical approaches has one or more of the disadvantages as summarized below: (i) low oxygen capacity; (ii) low $O_2$ uptake rate; (iii) formation of $\mu$-peroxo dimer; (iv) low chemical stability; and (v) relatively high synthesis cost. As a result, none of these approaches has yet been commercially used for gas separation and purification.

The use of metal complex-based adsorbents in the solid-state offers several advantages compared to their use in dilute solution. Metal complex-containing solutions have serious problems relating to metal complex solubility, solvent loss, and viscosity. However, owing to unfavorable molecular packing resulting in restricted access of oxygen molecules to vacant oxygen selective sites, solid-state adsorbents have been generally beset by insufficient oxygen capacities and slow oxygen uptake rates. Therefore, it is essential to create solid-state $O_2$-selective metal complex-based adsorbents with genuinely inherent microporous structures to decrease the mass transfer resistance.

U.S. Pat. No. 5,294,418 and EPO Application No. 0 853 976 A1 disclose two solid-state $O_2$-selective metal complex-based adsorbents. However, both of these adsorbents have disadvantages because of either unclear lifetimes or high costs of manufacture. The present invention describes novel solid state $O_2$-selective metal complex-based adsorbents which do not have these problems.

SUMMARY OF THE INVENTION

It is the primary object of the present invention to provide novel solid state $O_2$-selective metal complex-based adsorbents.

It is another object of the present invention to provide adsorption processes for separating oxygen from air or other gas mixtures to produce high purity nitrogen and/or argon.

It is a further object of the present invention to provide a novel adsorbent comprising a solid state $O_2$ selective metal complex, a porous support and an organic base polymer.

Additional objects and advantages of the invention will be set forth in part in the description which follows.

To achieve the foregoing objects and in accordance with the purposes of the present invention, the solid state $O_2$ selective metal complex adsorbent is selected from the group consisting of:

and wherein

R₁ and R₁', are selected from the group consisting of H, alkyl, perfluoroalkyl, aryl, alkyoxy, and mixtures thereof;

R₂ and R₂' are selected from the group consisting of H, hydroxy group, alkyl, perfluoalkyl, aryl, $Si(CH_3)_3$, Br, nitro, and mixtures thereof;

R₃ and R₃' are selected from the group consisting of H, hydroxyl group, alkyl, perfluoroalkyl, aryl, $Si(CH_3)_3$, Br, nitro, and mixtures thereof;

R₄ and R₄' are selected from the group consisting of H, alkyl, alkyoxy, nitro, halide, and mixtures thereof;

R₅ and R₅' are selected from the group consisting of H, $-C_6F_5$, $-C_6H_4$(p- and o-OH), $-C_6H_2$(2, 4, 6 trimethyl), $-C_6H_3$(2,6 di-Cl), $-C_6H_4$(p-Bu$^t$), $-C_6H_4$ (p- and o-NO₂), and mixtures thereof;

R₆ and R₆' are H;

R₇ and R₇' are selected from the group consisting of H, alkyl, alkyoxy, Br, nitro, and mixtures thereof;

R₈ and R₈' are selected from the group consisting of H, Br, nitro, and mixtures thereof;

R₁₀ and R₁₀' are selected from the group consisting of $-C_6F_5$, $-C_6H_4$(p- and o-OH), $-C_6H_2$(2, 4, 6 trimethyl), $-C_6H_3$(2, 6 di-Cl), $-C_6H_4$(p-Bu$^t$), $-C_6H_4$(p- and o-NO₂);

the ring is selected from the group consisting of 6-substituted phenoxide, 2-methoxy-6-substituted phenoxide, 3,5-di-tert-butyl-6-substituted phenoxide, 5-substituted pyrrole;

L is selected from the group consisting of $-C(CN)C(CN)-$, $-CH_2CH_2-$, $-C_6H_4-$, $-C_6H_2(CH_3)_2$, $-C_6H_{10}-$;

M is selected from the group consisting of $Co^{2+}$, $Fe^{2+}$, and $Mn^{2+}$;

D equals O, S, or N.

In another aspect of the present invention, the four-coordinate metal complexes are loaded onto a dual component support comprising organic base-containing polymer and porous material. Coordination of organic base-containing polymer to the metal complexes forms side-chain polymeric five-coordinate deoxy metal complex sites required for oxygen binding, and distributes $O_2$-selective metal complexes to improve mass transfer properties of the solid-state adsorbents. The porous material in a dual component support disperses the five-coordinate deoxy metal complex sites to further improve mass transfer properties, promoting heat transfer associated with adsorption and desorption, and facilitating the fabrication of secondary structured forms such as pellets or beads that may be desirable for their practicable use in commercial applications.

Porous materials suitable for the present invention include silica gel, alumina, activated carbon, carbon fiber, MCM-type mesoporous materials, and any other fibrous supports including polymers or inorganic materials. In addition, fibrous supports can be also laminated to achieve short transport pathways for gas transport in such composites.

The present invention will now be described in detail.

DETAILED DESCRIPTION OF THE INVENTION

This invention relates to solid state $O_2$-selective metal complex-based adsorbents and PSA, TSA or PSA/TSA adsorption processes that utilize these adsorbents. In particular, the adsorbents of the present invention comprise:

monomeric four-coordinate metal complexes (ML),
or oligomeric/polymeric four-coordinate metal complexes (MPL);
an organic base-containing polymer (PB);
a porous support (PS) and optionally an antioxidant

The new four-coordinate $O_2$-selective metal complexes of the present invention with low molecular mass significantly enhance the interaction of oxygen with $O_2$-selective metal centers owing to stronger electron donating ability of $N_4$ coordinating site. Some of the complexes also contain strong electron-withdrawing groups, e.g. CN, $NO_2$, in close proximity to $O_2$-selective metal centers to increase oxidation resistance of metal complex systems, including organic ligand and $O_2$-selective metal centers. For some types of metal complexes, bulky molecular moieties were built in to inhibit the formation of $\mu$-peroxo dimer.

In the practice of the present invention, four-coordinate main chain oligomeric/polymeric $O_2$-selective metal complexes including metalloporphyrin-containing and metal Schiff base-containing main chain oligomers/polymers have been utilized for the formation of the adsorbent. This combination can significantly increase chemical stability of $O_2$-selective metal complexes.

The above features give significant advantages over prior art materials with respect to tuning metal complex structures, oxygen loading capacity and rate, inhibiting formation of $\mu$-peroxo dimer, chemical stability, and synthesis cost. In addition, the adsorbents of the present invention are expected to show good performance in promoting heat transfer associated with adsorption and desorption, and facilitating the fabrication of secondary structured forms such as pellets or beads, etc., that may be desirable for commercial applications.

Procedure 1 set forth below outlines one general production process for the manufacture of solid-state $O_2$-selective metal complex-based adsorbents of the present invention starting from monomeric four-coordinate metal complexes (ML). Procedure 2 also set forth below shows one general production process using oligomeric/polymeric four-coordinate metal complexes (MPL).

Procedure 1

Description:
i: dispersion or coating;
ii: metallation;
iii: axial ligation

Procedure 2

Description:
a: dispersion or coating;
b: metallation;
c: polymerization;
d: axial ligation

Two important ratios are controlled in the production processes described above. The first ratio is weight ratio between porous materials and organic base-containing polymers (PB). The porous material should be kept to a minimum to achieve a workable oxygen loading in PSA, TSA or PSA/TSA process. The weight ratio can be from 1:1 to 1:3, and the preferred ratio is 1:2. The second ratio is the mole ratio between metal complexes (ML or MPL) and PB required to provide five-coordinate deoxy metal complex $O_2$-selective sites, which should be greater than one due to the usage of the base residues of said polymers in dispersion or coating processes. The mole ratio can be from 1:2 to 1:4, and the preferred one is 1:3.

In this invention, $N_2O_2$— and $N_4$-type chelating ligands including macrocycles and acyclic bidentate, tetradentate and other multidentate systems are used for developing solid state $O_2$-selective metal complex-based adsorbents. They can be porphyrins, Schiff bases and related ligand derivatives, five/six-membered heterocycle-containing ligand systems, and amidnate-type ligand systems.

To achieve the foregoing objects and in accordance with the purposes of the present invention, the solid state $O_2$ selective metal complex adsorbent is selected from the group consisting of:

and wherein $R_1$ and $R_1'$, are selected from the group consisting of H, alkyl, perfluoroalkyl, aryl, alkyoxy, and mixtures thereof;

$R_2$ and $R_2'$ are selected from the group consisting of H, hydroxy group, alkyl, perfluoalkyl, aryl, $Si(CH_3)_3$, Br, nitro, and mixtures thereof;

$R_3$ and $R_3'$ are selected from the group consisting of H, hydroxyl group, alkyl, perfluoroalkyl, aryl, $Si(CH_3)_3$, Br, nitro, and mixtures thereof;

$R_4$ and $R_4'$ are selected from the group consisting of H, alkyl, alkyoxy, nitro, halide, and mixtures thereof;

$R_5$ and $R_5'$ are selected from the group consisting of H, —$C_6F_5$, —$C_6H_4$(p- and o-OH), —$C_6H_2$(2, 4, 6 trimethyl), —$C_6H_3$(2,6 di-Cl), —$C_6H_4$(p-Bu$^t$), —$C_6H_4$ (p- and o-$NO_2$), and mixtures thereof;

$R_6$ and $R_6'$ are H;

$R_7$ and $R_7'$ are selected from the group consisting of H, alkyl, alkyoxy, Br, nitro, and mixtures thereof;

$R_8$ and $R_8'$ are selected from the group consisting of H, Br, nitro, and mixtures thereof;

$R_{10}$ and $R_{10}'$ are selected from the group consisting of —$C_6F_5$, —$C_6H_4$(p- and o-OH), —$C_6H_2$(2, 4, 6 trimethyl), —$C_6H_3$(2, 6 di-Cl), —$C_6CH_4$(p-Bu$^t$), —$C_6H_4$(p- and o-$NO_2$);

The ring is selected from the group consisting of 6-substituted phenoxide, 2-methoxy-6-substituted phenoxide, 3,5-di-tert-butyl-6-substituted phenoxide, 5-substituted pyrrole;

L is selected from the group consisting of —C(CN)C(CN)—, —CH$_2$CH$_2$—, —C$_6$H$_4$—, —C$_6$H$_2$(CH$_3$)$_2$, —C$_6$H$_{10}$—;

M is selected from the group consisting of Co$^{2+}$, Fe$^{2+}$, and Mn$^{2+}$;

D equals O, S, or N.

Procedure 3 shows three examples of metalloporphyrin-containing main-chain oligomeric/polymeric metal complexes used in this invention. Other metalloporphyrin precursors and coupling reagents are also included in this invention. For example, TPP(H$_2$)(F$_{20}$Cl$_8$), TPP(H$_2$)(Cl$_{20}$), and a coupling reagent, Br(CH$_2$)$_n$Br.

Example 1:

Description:
i: condensation;
ii: demethylation;
iii: metallation;
vi: polymerization M = Cu(II), Co(II), Fe(II), Ni(II), Mo(IV) etc.

Example 2:

Example 3:

Procedure 4 shows one example of metal Schiff base-containing main-chain oligomeric/polymeric metal complexes used in this invention. Other similar metal Schiff base precursors are also included in this invention. Moreover, $Br(CH_2)_nBr$ can also serve as a coupling reagent in polymerization.

Example 4:

Organic Base-Containing Polymers (PB)

One embodiment of the invention uses organic-base-containing polymers to load $O_2$-selective metal complexes, and control molecular packing in the solid state. By doing so, formation of highly crystalline phases of metal complexes is suppressed, and vacant $O_2$-selective sites become more accessible, which results in high oxygen loading at equilibrium. In addition, the polymer network may provide a certain porosity into the adsorbents, and a beneficial molecular packing to inhibit $\mu$-peroxo dimer formation.

Typical examples of organic base-containing polymers for production of solid-state $O_2$-selective metal complex-based adsorbents are polyvinylpyridine (PVPy) and its derivatives.

Porous Materials (PS)

This invention uses porous materials to further improve mass transfer properties of the solid-state adsorbents, to conduct heat transfer associated with adsorption and desorption, and to facilitate the fabrication of secondary structured forms such as pellets or beads that may be desirable for commercial applications.

The porous materials include silica gel, alumina, activated carbon, carbon fiber, MCM-type mesoporous materials, and any other fibrous supports either polymers or inorganic materials. They can be laminated to achieve short diffusion pathways for gas transport. The comparatively large pore size and surface area of such materials are used in this invention to maximally disperse metal complex-containing polymers into porous materials. However, they should be kept to a minimum to achieve a workable oxygen loading in PSA process.

In case of silica gel, thermal treatment is applied for removing adsorbed water molecules, and condensing the vicinal silanol groups or all surface Si—OH groups before use. This activation process offers a beneficial effect on dispersing or coating organic base-containing polymers on its surface.

The following examples are set forth below for purposes of illustration only.

EXAMPLE 1

Preparation of Bis(3,5-di-tert-butylsalicylidene)-1,2-(1,2-dicyanoacetylene)diamine (3,5-di-tert-ButSalMnH$_2$)

Diaminomaleonitrile (0.55 g, 5.09 mmol) was dissolved into toluene (20 ml). To it, a trace amount of acetic acid was added. It was found that diaminomaleonitrile was not completely soluble in toluene. Then, 3,5-di-tert-butylsalicylaldehyde (2.40 g, 10.24 mmol) dissolved into toluene (30 ml) was dropwise added into the above solution. The resulting solution was then heated at reflux under $N_2$ overnight. Next, all solvent was evaporated to dryness. The crude product was then purified by crystallization from $CH_2Cl_2$/hexane to give a yellow material. It was dried under vacuum. The yield was 1.1 g (40%). (Note: The yield was not optimized, and unreacted 3,5-di-tert-butylsalicylaldehyde was recycled.) $^1$H NMR (300 MHz, DMSO-d6): $\delta$=1.29 ppm (s, 18H), 1.42 ppm (m, 18H), 7.39 ppm (d, 2H), 7.50 ppm (d. 2H), 7.98 ppm (s, broad, 2×OH), 8.53 ppm (s, 2H); UV/Vis ($\lambda_{max}$, nm, in methanol): 273 (sh), 302, 337, 352, 385, 405 (sh); IR (cm$^{-1}$, nujol mull): 1608 (s, —C=N—), 2198 (s, —CN).

EXAMPLE 2

Preparation of Bis(3,5-di-tert-butylsalicylidene)-1,2-(1,2-dicyanoacetylene)diaminocobalt)II) [Co(3,5-di-tert-ButSalMn)]

Bis(3,5-di-tert-butylsalicylidene)-1,2-(1,2-dicyanoacetylene)diamine (3,5-di-tert-ButSalMnH$_2$) (1.03 g, 1.91 mmol) and cobalt acetate hydrate (0.47 g, 1.91 mmol) were dissolved into methanol (40 ml). To it, sodium hydroxide (0.15 g, 3.81 mmol) dissolved into methanol (10 ml) was added. Under $N_2$, the resulting solution was heated at reflux for 3 hours. Then, it was cooled down to room temperature, and a black solution was obtained. The product was not isolated, and the black solution was directly used for preparation of a composite of [Co(3,5-di-tert-ButSalMn)] with poly(4-vinylpyridine-co-styrene).

In another synthesis following the same procedure, the product was isolated by removing solvent and crystallization from acetone/hexanes. The yield was 91%. ESI MS: calcd. for $C_{34}H_{42}N_4O_2Co$, 597.67, found 597.5 (M$^+$).

EXAMPLE 3

Preparation of a Composite of poly(4-Vinylpyridine-co-styrene) (PVPy-co-styrene) with [Co(3,5-di-tert-ButSalMn)]

To above solution, poly(4-vinylpyridine-co-styrene) (0.22 g, 1.91 mmol of Py) was added under $N_2$. For solubility, anhydrous methanol (30 ml) was added into the solution. Next, the resulting solution was stirred at room temperature for 3 days. After removing all solvents, a black powder was obtained. It was dried under vacuum. The product contained sodium acetate as an impurity.

Adsorption properties of [Co(3,5-di-tert-ButSalMn)]-(PVPy-co-styrene)]

Figure 1:
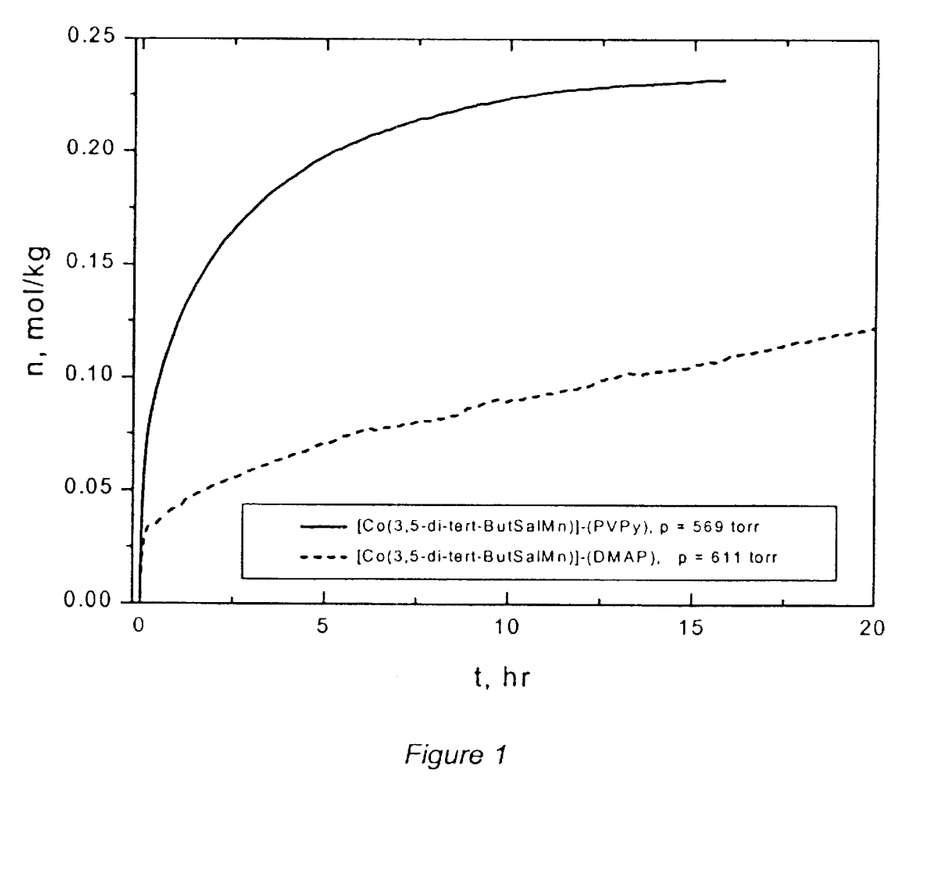
FIGS. 1 and 2 are a graphical representation of the $O_2$ uptake curve for two adsorbents of the present invention. DMAP represents 4-dimethyl-aminopyridine.

Adsorption studies were carried out using piezometric (constant volume-variable pressure) method at 20° C. The $O_2$ uptake rate curve was shown in FIG. 1. DMAP represents 4-dimethylaminopyridine.

EXAMPLE 4

Preparation of Bis(salicylidene)-1,2-ethylenediamine (SalenH$_2$)

Ethylenediamine (5.71 g, 0.095 mmol) was dissolved into toluene (60 ml). To it, a catalytic amount of acetic acid was added. Then, salicylaldehyde (23.20 g, 0.190 mmol) dissolved into toluene (60 ml) was dropwise added into the above solution. The resulting solution was then stirred at room temperature overnight. A yellowish crystalline product was precipitated. It was filtered, washed with ethanol, and dried. The yield was 23.7 g (93%). $^1$H NMR (300 MHz, CDCl$_3$): δ=3.84 ppm (s, 4H), 6.85 ppm (t, 2H), 6.92 ppm (d, 2H), 7.17 ppm (m. 2H), 7.19 ppm (m, 2H), 8.28 ppm (s, 2H), 12.77 (s, broad, 2×OH); ESI MS: calcd. for $C_{16}H_{16}N_2O_2$, 268.3, found 269.2 (M+1); UV/Vis ($\lambda_{max}$, nm, in methanol): 212, 255, 316, 400; IR (cm$^{-1}$, nujol mull): 1610 (m, —C=N—).

EXAMPLE 5

Preparation of Bis(Salicylidene)-1,2-ethylenediaminocobalt(II) [Co(Salen)]

Bis(Salicylidene)-1,2-ethylenediamine (SalenH$_2$) (22.7 g, 84.6 mmol) and cobalt acetate hydrate (21.1 g, 84.6 mmol) were dissolved into methanol (400 ml). Under $N_2$, the resulting solution was heated at reflux for 3 hours. Then, it was cooled down to room temperature, and deep brown crystalline product was precipitated out. The product was isolated by filtration, and dried. The yield was 24 g (87%).

EXAMPLE 6

Preparation of a Composite of Poly(4-vinylpyridine-co-styrene) with Silica Gel [(PVPy-co-styrene)/SiO$_2$)]

The styrene content in poly(4-vinylpyridine-co-styrene) was 10%. The specifications of silica gel used in the preparation were particle size, 70–230 mesh, pore size, 100 Å, and surface area 300 m$^2$/g. It was activated at 200° C. under $N_2$ for 10 hours.

Silica gel (200 g) and poly(4-vinylpyridine-co-styrene) (PVPy-co-styrene, 100 g) were well pre-mixed in solid state. The solid mixture was shaken at 80° C. overnight. Then toluene (1.4 liter) was added into the mixture, and the resulting mixture was continously shaken at room temperature overnight, forming a composite of poly(4-vinylpyridine-co-styrene) with silica gel. The composite was filtered and dried at 80° C. under vacuum. It was directly used for preparation of [Co(Salen)-(PVPy-co-styrene)]/SiO$_2$. Elemental analysis (average value, wt. %): C, 20.4; H, 2.1; N, 2.9. TGA analysis: The composite started to lose PVPy-co-styrene at 327° C. FT-IR (KBr pellet, cm$^{-1}$): 3423.6, 2920.9, 1639.5, 1598.4, 1554.6, 1415.6, 1101.6, 964.0, 816.5, 470.3. BET specific surface area analysis: 189 m$^2$/g.

EXAMPLE 7

Preparation of [Co(Salen)-(PVPy-co-styrene)]/SiO$_2$

Bis(salicylidene)-1,2-ethylenediaminocobalt(II) [Co(Salen)] (1.86 g, 5.7 mmol, mole ratio of pyridine to Co(Salen)=3:1) was mixed with the composite, [(PVPy-co-styrene)/SiO$_2$)] (6 g). The solid mixture was well ground, and then heated at 100° C. for 1 hour. It was cooled to room temperature, and then methanol (250 ml) was added. The resulting mixture was heated at reflux under $N_2$ overnight. Next, methanol was removed under a reduced pressure to dryness yielding a red-brown solid. The product was dried at 100° C. under vacuum. The yield was 7.8 g (99%). Elemental analysis (wt. %): C, 34.3; H, 3.1; N, 4.7; Co, 4.2. TGA analysis: The composite adsorbent significantly started to lose Co(Salen)/(PVPy-co-styrene) at 320° C. FT-IR (KBr pellet, cm$^{-1}$): 3431.3, 2923.6, 1631.6, 1600.4, 1531.2, 1450.1, 1101.5, 818.6, 757.2, 470.6. BET specific surface area analysis: 351 m$^2$/g.

Adsorption properties of [Co(Salen)-(PVPy-costyrene)]/SiO$_2$

Figure 2:
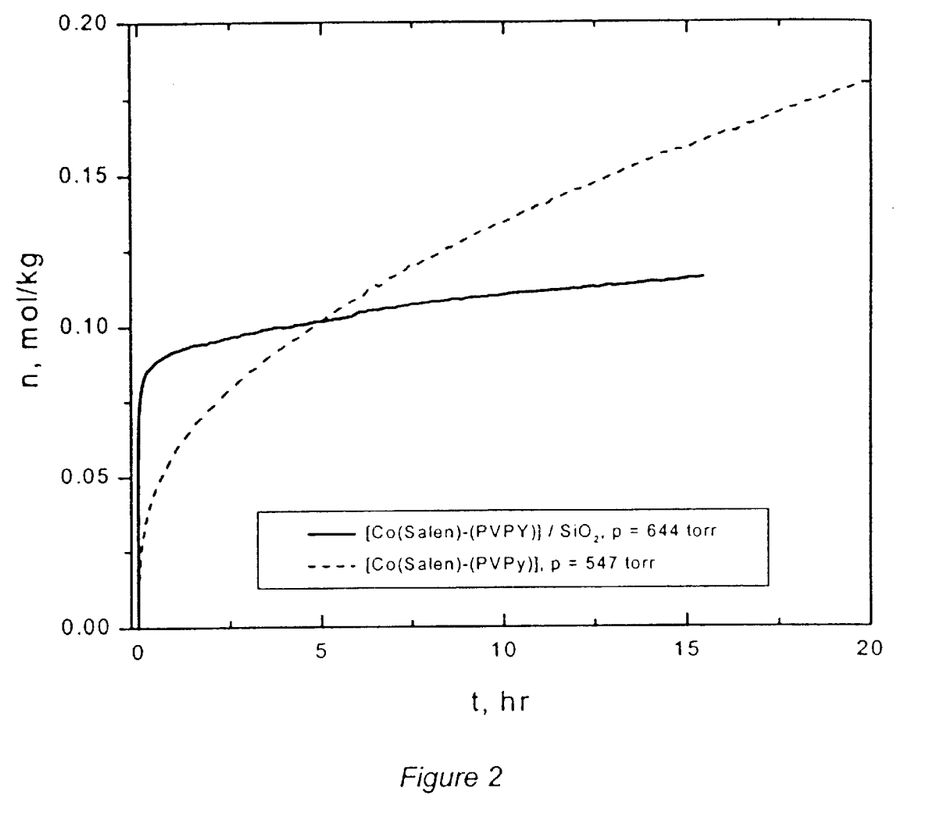

Adsorption studies were carried out using a piezometric method at 20° C. The $O_2$ uptake rate curve was shown in FIG. 2.

Having thus described the invention, what we claim is:

1. A process for the adsorption of oxygen from a feed gas comprising contacting said feed gas with a composite adsorbent comprising a four-coordinate metal complex, an organic base-containing polymer and a porous material.

2. The process as claimed in claim 1 wherein said solid state four-coordinate metal complex is selected from the group consisting of

-continued and wherein
R$_1$ and R$_1$', are selected from the group consisting of H, alkyl, perfluoroalkyl, aryl, alkyoxy, and mixtures thereof;
R$_2$ and R$_2$' are selected from the group consisting of H, hydroxy group, alkyl, perfluoalkyl, aryl, Si(CH$_3$)$_3$, Br, nitro, and mixtures thereof;
R$_3$ and R$_3$' are selected from the group consisting of H, hydroxyl group, alkyl, perfluoroalkyl, aryl, Si(CH$_3$)$_3$, Br, nitro, and mixtures thereof;
R$_4$ and R$_4$' are selected from the group consisting of H, alkyl, alkyoxy, nitro, halide, and mixtures thereof;
R$_5$ and R$_5$' are selected from the group consisting of H, —C$_6$F$_5$, —C$_6$H$_4$(p- and o-OH), —C$_6$H$_2$(2, 4, 6 trimethyl), —C$_6$H$_3$(2,6 di-Cl), —C$_6$H$_4$(p- and o-NO$_2$), and mixtures thereof;
R$_6$ and R$_6$' are H;
R$_7$ and R$_7$' are selected from the group consisting of H, alkyl, alkyoxy, Br, nitro, and mixtures thereof;
R$_8$ and R$_8$' are selected from the group consisting of H, Br, nitro, and mixtures thereof;
R$_{10}$ and R$_{10}$' are selected from the group consisting of —C$_6$F$_5$, —C$_6$H$_4$(p- and o-OH), —C$_6$H$_2$(2, 4, 6 trimethyl), —C$_6$H$_3$(2, 6 di-Cl), —C$_6$H$_4$(p-Bu$^t$), —C$_6$H$_4$(p- and o-NO$_2$);
the ring is selected from the group consisting of 6-substituted phenoxide, 2-methoxy-6-substituted phenoxide, 3,5-di-tert-butyl-6-substituted phenoxide, 5-substituted pyrrole;
L is selected from the group consisting of —C(CN)C(CN)—, —CH$_2$CH$_2$—, —C$_6$H$_4$—, —C$_6$H$_2$(CH$_3$)$_2$, —C$_6$H$_{10}$—;
M is selected from the group consisting of Co$^{2+}$, Fe2+, and Mn$^{2+}$;
D equals O, S, or N.
3. The process as claimed in claim 1 wherein said solid state four-coordinate metal complex is selected from the group consisting of wherein M is Mn(II), Co(II), Fe(II) and Ni(II), and n=1 to 10.

4. The process as claimed in claim 1 wherein said organic base-containing polymer is selected from the group consisting of polyvinylpyridine and its derivatives.

5. The process as claimed in claim 1 wherein said organic base-containing polymer is an organic base supported on an inorganic polymer selected from the group consisting of silica gel and MCM mesoporous materials.

6. The process as claimed in claim 1 wherein said porous material is selected from the group consisting of silica gel, alumina, activated carbon, carbon fiber, and MCM Mesoporous materials.

7. The process as claimed in claim 1 wherein the weight ratio of said porous material to said organic base-containing polymer is from about 1:1 to about 1:3.

8. The process as claimed in claim 1 wherein the mole ratio of said four-coordinate metal complex to said organic base-containing particles is from about 1:2 to about 1:4.

9. The process as claimed in claim 1 wherein said feed gas is air.

10. The process as claimed in claim 1 wherein said feed gas is a mixture of gases.

11. The process as claimed in claim 1 which is a pressure swing adsorption process.

12. The process as claimed in claim 1 which is a temperature swing adsorption process.

13. The process as claimed in claim 1 which is a pressure swing adsorption/temperature swing adsorption process.

14. A composite adsorbent comprising a solid state four-coordinate metal complex, an organic base-containing polymer and a porous material.

15. The composite adsorbent as claimed in claim 14 wherein said solid state four-coordinate metal complex is selected from the group consisting of

-continued wherein
- $R_1$ and $R_1'$, are selected from the group consisting of H, alkyl, perfluoroalkyl, aryl, alkyoxy, and mixtures thereof;
- $R_2$ and $R_2'$ are selected from the group consisting of H, hydroxy group, alkyl, perfluoalkyl, aryl, $Si(CH_3)_3$, Br, nitro, and mixtures thereof;
- $R_3$ and $R_3'$ are selected from the group consisting of H, hydroxyl group, alkyl, perfluoroalkyl, aryl, $Si(CH_3)_3$, Br, nitro, and mixtures thereof;
- $R_4$ and $R_4'$ are selected from the group consisting of H, alkyl, alkyoxy, nitro, halide, and mixtures thereof;
- $R_5$ and $R_5'$ are selected from the group consisting of H, $-C_6F_5$, $-C_6H_4$(p- and o-OH), $-C_6H_2$(2, 4, 6 trimethyl), $-C_6H_3$(2,6 di-Cl), $-C_6H_4$(p-Bu$^t$), $-C_6H_4$(p- and o-$NO_2$), and mixtures thereof;
- $R_6$ and $R_6'$ are H;
- $R_7$ and $R_7'$ are selected from the group consisting of H, alkyl, alkyoxy, Br, nitro, and mixtures thereof;
- $R_8$ and $R_8'$ are selected from the group consisting of H, Br, nitro, and mixtures thereof;
- $R_{10}$ and $R_{10}'$ are selected from the group consisting of $-C_6F_5$, $-C_6H_4$(p- and o-OH), $-C_6H_2$(2, 4, 6 trimethyl), $-C_6H_3$(2, 6 di-Cl), $-C_6H_4$(p-Bu$^t$), $-C_6H_4$(p- and o-$NO_2$);
- the ring is selected from the group consisting of 6-substituted phenoxide, 2-methoxy-6-substituted phenoxide, 3,5-di-tert-butyl-6-substituted phenoxide, 5-substituted pyrrole;
- L is selected from the group consisting of $-C(CN)C(CN)-$, $-CH_2CH_2-$, $-C_6H_4-$, $-C_6H_2(CH_3)_2$, $-C_6H_{10}-$;
- M is selected from the group consisting of $Co^{2+}$, $Fe^{2+}$, and $Mn^{2+}$;
- D equals O, S, or N.

16. The composite adsorbent as claimed in claim 14 wherein said solid state four-coordinate metal complex is selected from the group consisting of -continued wherein M is Mn(II), Co(II), Fe(II) and Ni(II), and n=1 to 10.

17. The composite adsorbent as claimed in claim 14 wherein said organic base-containing polymer is selected from the group consisting of polyvinylpyridine and its derivatives.

18. The composite adsorbent as claimed in claim 14 wherein said organic base-containing polymer is an organic base supported on an inorganic polymer selected from the group consisting of silica gel and MCM mesoporous materials.

19. The composite adsorbent as claimed in claim 14 wherein said porous material is selected from the group consisting of silica gel, alumina, activated carbon, carbon fiber, and MCM mesoporous materials.

20. The composite adsorbent as claimed in claim 14 wherein the weight ratio of said porous material to said organic base-containing polymer is from about 1:1 to about 1:3.

21. The composite adsorbent as claimed in claim 14 wherein the mole ratio of said four-coordinate metal complex to said organic base-containing particles is from about 1:2 to about 1:4.

* * * * *